US012653772B2

(12) United States Patent (10) Patent No.: US 12,653,772 B2

Clabault (45) Date of Patent: Jun. 16, 2026

(54) USE OF A ROSEBUSH EXTRACT AS DEPIGMENTING ACTIVE AGENT

(71) Applicant: L'OREAL, Paris (FR)

(72) Inventor: Chloé Clabault, Chevilly Larue (FR)

(73) Assignee: L'OREAL, Paris (FR)

( * ) Notice: Subject to any disclaimer, the term of this patent is extended or adjusted under 35 U.S.C. 154(b) by 255 days.

(21) Appl. No.: 18/256,663

(22) PCT Filed: Dec. 13, 2021

(86) PCT No.: PCT/EP2021/085539

§ 371 (c)(1),
(2) Date: Jun. 9, 2023

(87) PCT Pub. No.: WO2022/128943

PCT Pub. Date: Jun. 23, 2022

(65) Prior Publication Data

US 2024/0033210 A1      Feb. 1, 2024

(30) Foreign Application Priority Data

Dec. 17, 2020    (FR) ...................................... 2013457

(51) Int. Cl.
*A61K 36/00*        (2006.01)
*A61K 8/9789*        (2017.01)
*A61Q 19/02*        (2006.01)

(52) U.S. Cl.
CPC ............ *A61K 8/9789* (2017.08); *A61Q 19/02* (2013.01); *A61K 2800/805* (2013.01)

(58) Field of Classification Search
CPC ...................................................... A61Q 19/02
See application file for complete search history.

(56) References Cited

U.S. PATENT DOCUMENTS

2020/0178431 P1      6/2020   Delbard

FOREIGN PATENT DOCUMENTS

| CN | 108030744 | A | 5/2018 |
| KR | 100389096 | B1 | 6/2003 |
| WO | 2022128943 | A1 | 6/2022 |

OTHER PUBLICATIONS

International Search Report and Written Opinion dated Feb. 14, 2022 from International Application No. PCT/EP2021/085539 with filing date Dec. 13, 2021; 11 pages.
Database GNPD [Online]; Mintel; "Revitalizing Brightening Velvet Cream SPF 15", XP055828313, ID No. 7973045; Aug. 3, 2020; 8 pages.

*Primary Examiner* — Qiuwen Mi

(74) *Attorney, Agent, or Firm* — Womble Bond Dickinson (US) LLP

(57)        ABSTRACT

The present invention relates to a non-therapeutic cosmetic use of an extract of a hybrid rosebush obtained by crossing of varieties Meichibon x Delgramaue, as depigmenting and/or lightening and/or whitening active agent.
The present invention also relates to a non-therapeutic cosmetic process for depigmenting, lightening and/or whitening keratin materials, in particular the skin, comprising the application of a cosmetic composition comprising, in a physiologically acceptable medium, an extract of a hybrid rosebush obtained by crossing of varieties Meichibon x Delgramaue.

18 Claims, 2 Drawing Sheets

[Fig. 1]

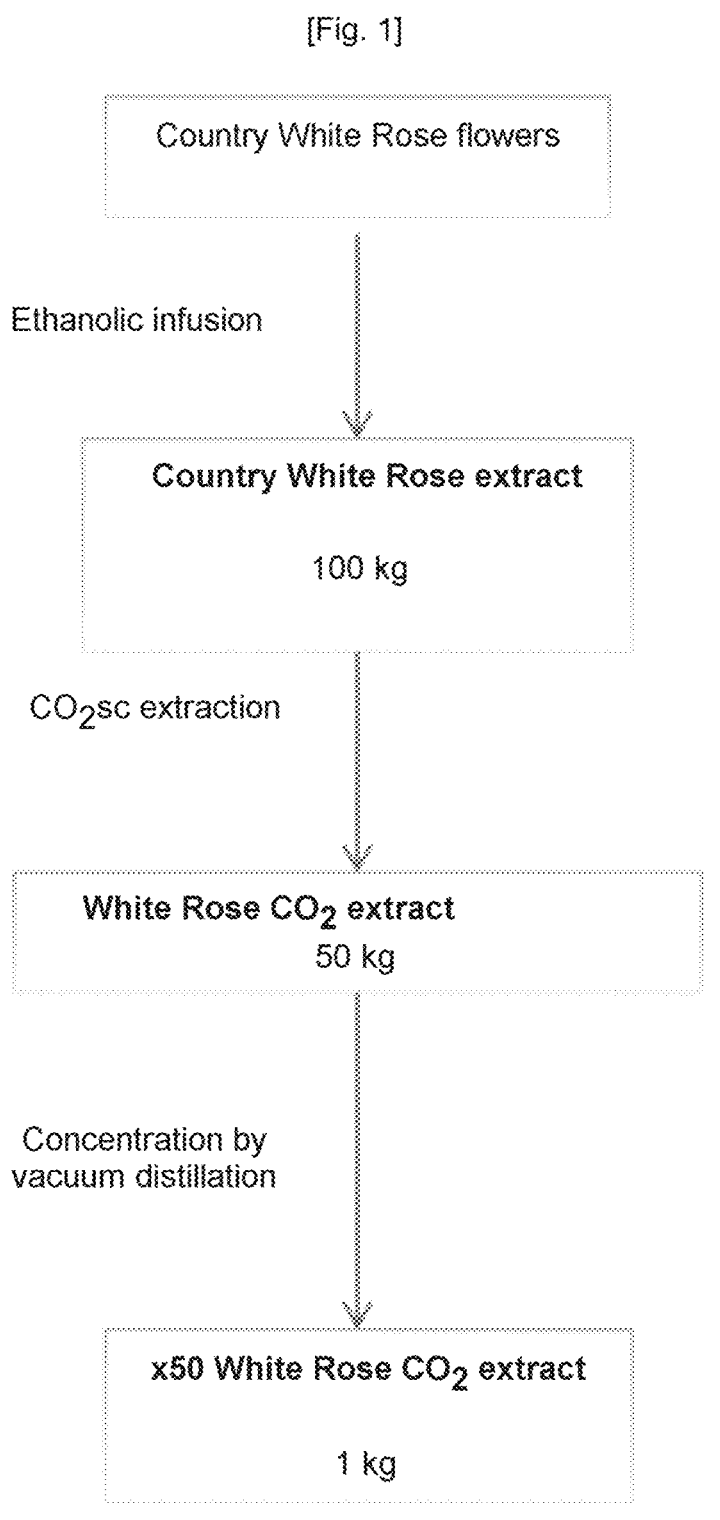

Country White Rose flowers

Ethanolic infusion

Country White Rose extract 100 kg $CO_2$sc extraction

White Rose $CO_2$ extract
50 kg

Concentration by
vacuum distillation x50 White Rose $CO_2$ extract 1 kg

[Fig. 2]
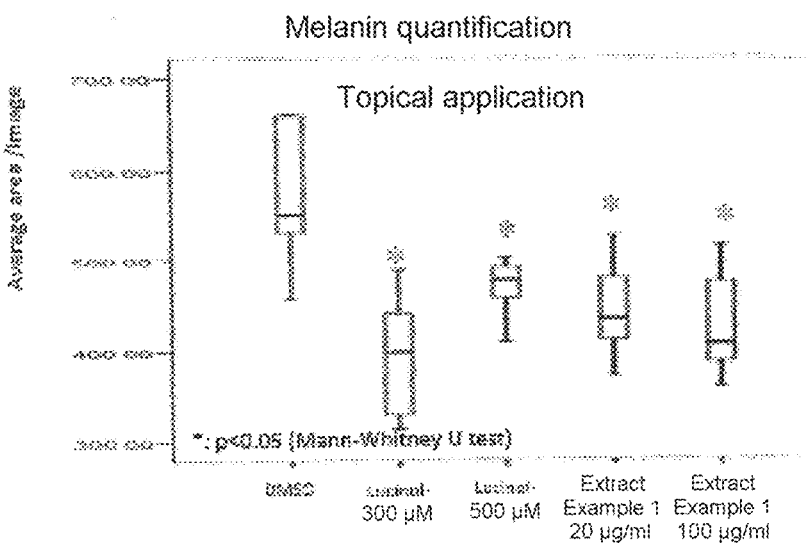
Melanin quantification
Topical application
*: p<0.05 (Mann-Whitney U test)

USE OF A ROSEBUSH EXTRACT AS DEPIGMENTING ACTIVE AGENT

The present invention relates to the field of active agents dedicated to the care of keratin materials, such as the skin or the skin appendages.

The present invention relates to a non-therapeutic cosmetic use of an extract of a hybrid rosebush obtained by crossing of varieties Meichibon x Delgramaue, as depigmenting and/or lightening and/or whitening active agent.

The present invention also relates to a non-therapeutic cosmetic process for depigmenting, lightening and/or whitening keratin materials, in particular the skin, comprising the application of a cosmetic composition comprising, in a physiologically acceptable medium, an extract of a hybrid rosebush obtained by crossing of varieties Meichibon× Delgramaue.

At various periods of their life, some people see the appearance on their skin, and more particularly on their hands, of darker and/or more coloured spots, which give the skin heterogeneity. These blemishes are especially due to a high concentration of melanin in the keratinocytes located at the surface of the skin.

The use of highly effective inoffensive topical depigmenting substances is most particularly sought for the purpose of treating pigmentary blemishes.

The mechanism of formation of the pigmentation of the skin, i.e. of the formation of melanin, is particularly complex and involves, schematically, the following main steps:

Tyrosine->Dopa->Dopaquinone->Dopachrome->Melanin

Tyrosinase (monophenol dihydroxyl phenylalanine: oxygen oxidoreductase EC 1.14.18.1) is the essential enzyme involved in this sequence of reactions. In particular, it catalyses the conversion reaction of tyrosine to give dopa (dihydroxyphenylalanine), by virtue of its hydroxylase activity, and the conversion reaction of dopa to give dopaquinone, by virtue of its oxidase activity. This tyrosinase acts only when it is in mature form under the effect of certain biological factors.

A substance is acknowledged as being depigmenting if it acts directly on the vitality of the epidermal melanocytes where melanogenesis takes place, and/or if it interferes with one of the steps of melanin biosynthesis, either by inhibiting one of the enzymes involved in melanogenesis, or by inserting itself as a structural analogue of one of the chemical compounds of the melanin synthesis chain, which chain can then be blocked, thus ensuring depigmentation.

Lucinol is known as a skin-depigmenting agent.

Thus, substances which have an efficient depigmenting action, in particular at least similar to or even greater than lucinol, were sought.

In this regard, the applicant has, surprisingly and unexpectedly, discovered that an extract of a hybrid rosebush obtained by crossing of varieties Meichibon x Delgramaue exhibits good depigmenting activity.

A subject of the invention is thus a non-therapeutic cosmetic process for depigmenting, lightening and/or whitening keratin materials, in particular the skin, comprising the application of a cosmetic composition comprising, in a physiologically acceptable medium, an extract of a hybrid rosebush obtained by crossing of varieties Meichibon x Delgramaue as defined below.

The invention also relates to the non-therapeutic cosmetic use of an extract of a hybrid rosebush obtained by crossing of varieties Meichibon x Delgramaue, as an agent for whitening, lightening and/or depigmenting keratin materials, in particular the skin.

The extract of a hybrid rosebush obtained by crossing of varieties Meichibon x Delgramaue, used according to the invention, makes it possible to efficiently depigment and/or lighten, or even whiten, human skin. It is in particular intended to be applied to the skin of individuals having a dull complexion, a non-uniform complexion, brownish pigmentation blemishes or liver spots, or to the skin of individuals wishing to combat the appearance of a brownish colour caused by melanogenesis.

Said extract may also make it possible to depigment and/or lighten bodily hairs, the eyelashes, head hair, and also the lips and/or the nails.

A subject of the invention is also the non-therapeutic cosmetic use of an extract of a hybrid rosebush obtained by crossing of varieties Meichibon x Delgramaue as described above, as an agent for whitening and/or lightening and/or depigmenting the skin, bodily hairs, the eyelashes or head hair, and also the lips and/or the nails, and preferably the skin, in particular for making the complexion uniform, improving the radiance of the complexion, eliminating pigmentation spots or senescence spots, and/or as anti-tanning agents.

DETAILED DESCRIPTION

Rosebush Extract

Preferably, said rosebush extract may be obtained from flowers, flowering heads and/or leaves of said rosebush.

Preferably, said rosebush extract may be obtained by extraction with supercritical $CO_2$ of an alcoholic mixture of all or part of said rosebush.

Preferably, said rosebush extract may be characterized in that said alcoholic mixture is obtained after infusion of all or part of said rosebush in at least one bath comprising an alcoholic solvent, at a temperature of less than 50° C., in order to obtain an alcoholic mixture.

The variety name Meichibon refers to a rosebush belonging to the family Rosaceae, from the genus Rosa. It is a hybrid tea rose, also commercially referred to as Tchaikovski®, or Tchaikovski® Meichibon, rosebush or Meilland rosebush.

The variety name Delgramaue refers to a rosebush belonging to the family Rosaceae, from the genus Rosa, from the species *Floribunda*, also commercially referred to as "rose synactif by Shisheido®" (Delbard), or "La Rose du Petit Prince".

Such a hybrid rosebush may present abundant white double leaves, which may show some pink-coloured tips, i.e. an average of five flowers per stem, and also a fragrance presenting various notes, including (i) a top note of grapefruit and citrus rose, (ii) a heart note of apricot and lychee and (iii) a green base note. It may reach, on average, a height of about 70 to 80 cm, and a width of about 40 to 50 cm, with branches having a diameter of between about 8 and 10 mm.

In particular, such a hybrid rosebush may be obtained by hybridization of a "male" variety of the variety name Delgramaue, and of a "female" variety of the variety name Meichibon.

In particular, such a hybrid rosebush may be obtained by pollination, i.e. application of a pollen from the stamens of a "male" flower, and in particular of a flower belonging to the variety name Delgramaue, on the pistil of a "female" flower, and in particular of a flower belonging to the variety name Meichibon.

This hybrid rosebush may notably be distinguished from the varieties Meichibon and Delgramaue, defined previously, by virtue of a combination of the following features:

the number of petals generally differs from the Meichibon variety, in that this type of rosebush has flowers with a greater number of petals, of a bigger size, and with a stronger fragrance with, as stated previously, a characteristic note of grapefruit;

the colour of the petals generally differs from the Delgramaue variety, in that their colour is generally white, whereas the Delgramaue variety has petals of a lilac colour; it is more vigorous and more resistant to the disease known as "black spot disease of roses".

A supercritical $CO_2$ extract generally refers to an extract obtained by a process using $CO_2$ gas in a "supercritical" state, i.e. at a high pressure level (generally greater than 50 bar, or even greater than 70 bar), and at a low temperature (generally greater than 30° C. and lower than 50° C.).

According to one embodiment, the extraction is performed in the presence of a $CO_2$ gas in the supercritical state, i.e. at a temperature of at least 31.1° C. and at a pressure of at least 74.5 bar.

Said supercritical $CO_2$ extract may notably be obtained according to a protocol described in WO 2012/085366 and detailed hereinbelow.

The term "keratin materials" is intended to denote the skin and its integuments, notably the scalp, the hair follicles and keratin fibres, notably head hair, the eyebrows, the eyelashes, and beard and moustache hair.

The term "skin" means all of the skin of the body, including the scalp, mucous membranes, semimucous membranes, and the skin integuments.

The term "skin integuments" means bodily hair, the eyelashes, head hair and the nails. More particularly, in the present invention, head hair, the skin of the neckline, of the neck and of the face, the eyelashes and the eyebrows are considered.

The term "preventing" also means "reducing the probability of occurrence or of recurrence of a phenomenon".

Rosebush extracts according to the invention may be obtained from plant material derived from whole plants or from plant parts, such as the leaves, stems, flowers, flowering heads, petals, sepals or roots cultivated in vivo or in vitro.

The term "in vivo cultivation" means any cultivation of conventional type, i.e. in soil in the open air or in a greenhouse, or alternatively out of the soil.

The term "in vitro cultivation" means all the techniques known to those skilled in the art which make it possible to artificially obtain a plant or a plant part. The imposed selection pressure makes it possible to obtain a plant material which is standardized and available all year round, contrary to plants cultivated in vivo.

In particular, said rosebush extract may be obtained from flowers, flowering heads, and/or leaves.

Formulations

Extracts according to the invention may be formulated in any cosmetic compositions, notably for application to the skin, the nails or the mucous membranes. Depending on the retained administration method, a composition of the invention may be in any of the presentation forms normally used.

A composition according to the invention comprises a physiologically acceptable medium.

The term "physiologically acceptable medium" means a medium that is compatible with keratin materials, in particular the skin. According to one embodiment, an extract according to the invention may be administered via a topical route.

According to one preferred embodiment, the rosebush extract according to the invention may be is present, in said composition, in a concentration of between 0.0001% and 10% by weight of said extract, relative to the total weight of the composition, preferably between 0.001% and 5% by weight of said extract, even better still between 0.01% and 2% by weight of said extract relative to the total weight of the composition.

Advantageously, the extracts according to the invention may be formulated or dissolved in water or a water-soluble organic solvent, or a mixture thereof.

A water-soluble organic solvent that is suitable for use in the invention may be chosen from lower monoalcohols including from 2 to 8 atoms, and $C_2$ to $C_8$, preferably $C_3$ to $C_8$, hydrocarbon-based compounds comprising from 2 to 6 hydroxyl groups, preferably from 3 to 5 hydroxyl groups, and mixtures thereof.

Among the water-soluble organic solvents that are suitable for use in the invention, mention may notably be made of glycols containing from 2 to 8 carbon atoms, such as ethylene glycol, propylene glycol or 1,3-propanediol, 1,3-butylene glycol, dipropylene glycol, glycerol, sorbitol, and mixtures thereof. Preferably, propylene glycol or 1,3-propanediol is most particularly suitable for use in the invention.

Among the lower monoalcohols, mention may in particular be made of those including from 2 to 6 carbon atoms, such as ethanol, isopropanol, propanol or butanol.

In a preferred embodiment, the water-soluble organic solvent is ethanol.

A water-soluble organic solvent may constitute from 20% to 90% by weight of the composition containing it, preferably from 30% to 80%, preferably from 40% to 70%, and more preferably from 50% to 60% by weight of the composition containing it.

A water that is suitable for use in the invention may be a spring and/or mineral water, notably chosen from Vittel water, waters from the Vichy basin and La Roche Posay water. A water that is suitable for use in the invention may also be a floral water, such as rose water.

Water may constitute from 20% to 90% by weight of the composition containing it, preferably from 30% to 80%, preferably from 40% to 70%, and more preferably from 50% to 60% by weight of the composition containing it. Advantageously, water constitutes up to 50% by weight of the composition containing it.

For topical application to keratin materials, and notably the skin or its integuments, a composition may notably be in the form of an aqueous or oily solution or of a dispersion of the lotion or serum type, of emulsions of liquid or semi-liquid consistency of the milk type, obtained by dispersing a fatty phase in an aqueous phase (O/W), or conversely (W/O), or of suspensions or emulsions of soft consistency, of the aqueous or anhydrous gel or cream type, or else of microcapsules or microparticles, or of vesicular dispersions of ionic and/or non-ionic type. These compositions are prepared according to the usual methods.

These compositions may constitute cleansing, protective, treating or care creams for the face, the hands, the feet, the major anatomical folds or the body (for example day creams, night creams, makeup creams, makeup-removing creams, foundation creams or antisun creams), fluid foundations, makeup compositions such as makeup-removing milks, protective or care body milks, antisun milks, skincare lotions, gels or foams, for instance cleansing lotions, antisun lotions, artificial tanning lotions, bath compositions, deodorant compositions comprising a bactericidal agent, aftershave gels or lotions, or hair-removing creams. These compositions may also be constituted of solid preparations constituting soaps or cleansing bars or may be packaged in the form of an aerosol composition also comprising a pressurized propellant.

According to one embodiment, a composition according to the invention may comprise:

at least one oil, such as a volatile oil, and notably a volatile hydrocarbon-based oil; and/or at least one fatty substance, such as a fatty substance which is solid at 25 C.

The amounts of the various constituents in the compositions according to the invention are those conventionally used in the fields under consideration.

When a composition is an emulsion, the proportion of the fatty phase may range from 5% to 80% by weight and preferably from 5% to 50% by weight relative to the total weight of the composition. The oils, waxes, emulsifiers and coemulsifiers used in a composition in emulsion form are chosen from those conventionally used in the cosmetics field. The emulsifier and the coemulsifier may be present, in a composition, in a proportion ranging from 0.3% to 30% by weight and preferably from 0.5% to 20% by weight relative to the total weight of the composition.

When a composition is an oily solution or gel, the fatty phase may represent more than 90% of the total weight of the composition.

In a known manner, a cosmetic composition of the invention may also contain adjuvants that are customary in the cosmetics field, such as hydrophilic or lipophilic gelling agents, hydrophilic or lipophilic additives, preservatives, antioxidants, solvents, fragrances, fillers, screening agents, odour absorbers and colorants. The amounts of these various adjuvants are those conventionally used in the cosmetics field, and are, for example, from 0.01% to 10% of the total weight of the composition. Depending on their nature, these adjuvants may be introduced into the fatty phase, into the aqueous phase and/or into lipid spherules.

As oils or waxes that may be used in the invention, mention may be made of mineral oils (liquid petroleum jelly), plant oils (liquid fraction of shea butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils.

As emulsifiers that may be used in the invention, mention may be made, for example, of glyceryl stearate, polysorbate 60, and the PEG-6/PEG-32/glycol stearate mixture sold under the name Tefose® 63 by the company Gattefosse.

As solvents that may be used in the invention, mention may be made of lower alcohols, notably ethanol, isopropanol and propylene glycol.

As hydrophilic gelling agents that may be used in the invention, mention may be made of carboxyvinyl polymers (carbomer), acrylic copolymers such as acrylate/alkyl acrylate copolymers, polyacrylamides, polysaccharides such as hydroxypropylcellulose, natural gums, preferably xanthan gum, and clays, and, as lipophilic gelling agents, mention may be made of modified clays such as bentones, metal salts of fatty acids, for instance aluminium stearates, and hydrophobic silica, ethylcellulose and polyethylene.

A hybrid rosebush extract according to the invention, obtained by crossing the varieties Meichibon x Delgramaue, may be obtained by any known means.

For example, an extract according to the invention may be obtained by extraction with apolar volatile solvents derived from petrochemistry, such as hexane, isohexane, cyclohexane, benzene, petroleum ether, propane or butane. The water from the plants is then allowed to settle, and the solvent containing the perfume is concentrated under vacuum to yield the extracted perfume essence. An extract according to the invention may also be obtained by steam distillation or by hydrodistillation.

Said extract may be an alcoholic mixture obtained by infusing all or part of said rosebush in at least one bath comprising an alcoholic solvent.

Production Process

The general process of extraction with supercritical $CO_2$ is known. In the supercritical state, i.e. at more than 74 bar (in particular at more than 74.4 bar) and more than 31° C. (in particular at more than 31.1° C.), $CO_2$ has very special properties and may be used as a natural extraction solvent. The obtained fluid is characterized by high diffusivity (of the order of that of gases) which gives it good ability for diffusion, and a high density which imparts a high capacity for transport and extraction.

In a preferred manner, a rosebush extract according to the invention is obtained by an extraction process with supercritical $CO_2$ of all or part of said rosebush, and notably according to any one of the variants described in WO 2012/085366, the contents of which are incorporated by reference in the present description.

According to this preferred embodiment, said rosebush extract may thus be obtained by extraction with supercritical $CO_2$ of an alcoholic mixture of all or part of said rosebush. Said alcoholic mixture may also be obtained by infusing all or part of said rosebush in at least one bath comprising an alcoholic solvent.

The extraction step with supercritical $CO_2$ according to the invention may be performed in static mode or in dynamic mode.

According to the invention, the $CO_2$ is preferentially used at a pressure of between 130 and 200 bar and at a temperature of between 35 and 55° C., even more preferentially at 150 bar and 45° C., in counter-current mode, and is particularly suitable for obtaining an extract of fresh flowers and/or leaves, which is clear, transparent and stable, mostly freed of sugars, colorants, and water, and having an alcohol titer of at least 75%.

Advantageously, the process according to the invention also comprises a step in which the extract obtained after extraction with supercritical $CO_2$ is concentrated as obtained, under vacuum with mild heating at a temperature of less than 60° C., or on a support such as a natural oil, shea butter, natural glycerol, or a natural fragrant molecule such as natural benzyl acetate, natural geraniol, or natural nerolidol.

As an example of an alcoholic solvent according to the invention, a natural alcohol chosen from methanol, ethanol, 1-propanol, 2-propanol, butanol, isobutanol, pentanol and isoamyl alcohol, preferentially ethanol, is used, which has a lower boiling point (except for methanol) and which is much less toxic than, notably, methanol. An alcoholic solvent may be an ethanolic solvent.

Most particularly, said alcoholic mixture may be obtained after infusion of flowers, flowering heads, and/or leaves in at least one bath comprising an alcoholic solvent, at a temperature of less than 50° C., in order to obtain an alcoholic or aqueous-alcoholic mixture, or even a fragranced alcoholic or aqueous-alcoholic mixture.

According to the invention, the flowers, flowering heads and/or leaves are preferentially infused in the alcoholic solvent at ambient temperature, i.e. a temperature of between 15 and 35° C.

An alcoholic mixture may thus be obtained by infusing all or part of said rosebush in at least one bath comprising an alcoholic solvent.

A rosebush extract according to the invention may notably comprise volatile compounds, and in particular at least one compound chosen from: cis-3-hexenol, trans-2-hexenol, $C_6$ alcohol, diethoxyethanol, methylheptenone, acetin or a related compound, cis-3-hexenyl acetate, hexyl acetate, phenylacetaldehyde, benzyl alcohol, linanol, phenylethyl alcohol, diacetin or a related compound, benzyl acetate, diethyl succinate, terpinen-4-ol, nerol, citronellol, geraniol, geranial, cistheaspirane, delta-elemene, citronellyl acetate, geranyl acetate, alpha-copaene, beta-elemene, coumarin, hydroxyedulane or isomer, $\beta$-caryophyllene, dihydro-$\beta$-ionin, dihydro-$\beta$-ionol, $\alpha$-jumulene, $\gamma$-muurolene, germacrene D, $\alpha$-cadinene, $\beta$-bisabolene, $\gamma$-cadinene, $\gamma$-eudesmol, $\beta$-eudesmol, $\alpha$-cadinol, 4-oxo-dihydro-$\beta$-ionol, benzyl benzoate, ethyl myristate, $C_{19}$ alkene, $C_{19}$ alkane, palmitic acid, ethyl palmitate, $C_{20}$ alkane, $C_{21}$ alkane, linoleic acid, linolenic acid, ethyl linoleate, ethyl linolenate, ethyl stearate, tricosene, tricosane, dihydro-$\beta$-ionol ester.

In particular, a rosebush extract according to the invention may notably comprise a plurality of compounds chosen from: cis-3-hexenol, trans-2-hexenol, $C_6$ alcohol, diethoxyethanol, methylheptenone, acetin or a related compound, cis-3-hexenyl acetate, hexyl acetate, phenylacetaldehyde, benzyl alcohol, linanol, phenylethyl alcohol, diacetin or a related compound, benzyl acetate, diethyl succinate, terpinen-4-ol, nerol, citronellol, geraniol, geranial, cistheaspirane, delta-elemene, citronellyl acetate, geranyl acetate, alpha-copaene, beta-elemene, coumarin, hydroxyedulane or isomer, $\beta$-caryophyllene, dihydro-$\beta$-ionin, dihydro-$\beta$-ionol, $\alpha$-jumulene, $\gamma$-muurolene, germacrene D, $\alpha$-cadinene, $\beta$-bisabolene, $\gamma$-cadinene, $\gamma$-eudesmol, $\beta$-eudesmol, $\alpha$-cadinol, 4-oxo-dihydro-$\beta$-ionol, benzyl benzoate, ethyl myristate, $C_{19}$ alkene, $C_{19}$ alkane, palmitic acid, ethyl palmitate, $C_{20}$ alkane, $C_{21}$ alkane, linoleic acid, linolenic acid, ethyl linoleate, ethyl linolenate, ethyl stearate, tricosene, tricosane, dihydro-$\beta$-ionol ester.

A rosebush extract according to the invention, notably obtained by extraction with supercritical $CO_2$, may, for example, comprise at least one compound chosen from: geraniol, geranial, nerol and citronellol.

According to one embodiment, a rosebush extract according to the invention may also comprise at least one compound chosen from: cis- or trans-theaspirane, dihydro-beta-ionone, dihydro-beta-ionol, 4-oxodihydronetaionol.

During infusion, the flowers, flowering heads and/or leaves are soaked in the alcoholic solvent and may be gently swirled.

Advantageously, the infusion is performed using solvent circulation in a closed circuit, i.e. the solvent is circulated on the flowers, flowering heads and/or leaves so as to create a movement in the extractor, notably without breaking the petals, and to avoid saturation areas of the solvent around the petals. The swirling thus provides solvent which is less saturated and which will in turn perform the extraction. Alternatively, infusions may be performed in several concomitant or successive baths, depending on the amount of flowers and/or leaves to be treated.

It is possible, for example, to prepare a single bath, followed by rinsing using fresh extraction solvent, several baths with the same flowers and/or leaves, or even several runs of flowers and/or leaves in the same bath due to the low saturation of the ethanol, for a final weight/weight ratio of flowers-leaves/alcoholic solvent of from 1:1 to 1:10, preferentially from 1:1 to 1:3.

For example, advantageously several reruns of flowers and/or leaves may be performed in the same alcoholic bath in order to saturate it, for example up to five reruns, which makes it possible to concentrate the primary alcoholic extract. This proves to be more economical in terms of volumes to be transported and treated when the process for obtaining said extract involves an extraction step with supercritical $CO_2$.

Next, according to the process, the flowers, flowering heads and/or leaves are generally drained, avoiding excessive crushing, and the alcoholic mixture thus obtained is filtered so as to collect an alcoholic floral infusion suitable for keeping cool at a temperature from about 4 to 10° C. for one day to several months.

Thus, a process for obtaining a rosebush extract can comprise the following steps:

a) infusing all or part of a hybrid rosebush obtained by crossing of varieties Meichibon x Delgramaue, in at least one bath comprising an alcoholic solvent, in particular an ethanolic solvent, at a temperature of less than 50° C., so as to obtain an alcoholic mixture;

b) optionally filtering said alcoholic mixture so as to recover an alcoholic floral infusion; and c) carrying out an extraction with supercritical $CO_2$ of said alcoholic mixture or of said alcoholic floral infusion so as to obtain said extract.

A process for obtaining a rosebush extract can comprise the following steps:

a) picking the flowers, flowering heads and/or leaves of a hybrid rosebush obtained by crossing of varieties Meichibon x Delgramaue;

b) infusing the flowers, flowering heads and/or leaves provided in step a), in at least one bath comprising an alcoholic solvent, in particular an ethanolic solvent, at a temperature of less than 50° C., so as to obtain an alcoholic mixture;

c) optionally filtering said alcoholic mixture so as to recover an alcoholic floral infusion; and d) carrying out an extraction with supercritical $CO_2$ of said alcoholic mixture or of said alcoholic floral infusion so as to obtain said extract.

Throughout the description, including the claims, the term "comprising a" should be understood as being synonymous with "comprising at least one", unless otherwise specified.

In addition, the term "at least one" should be understood as being synonymous with "one or more", unless otherwise specified.

The expressions "more than", "between . . . and . . . " and "ranging from . . . to . . . " should be understood as being limits inclusive, unless otherwise specified.

The examples and figures that follow are presented as nonlimiting illustrations of the invention. The compounds are, depending on the case, cited as the chemical names or as the CTFA (International Cosmetic Ingredient Dictionary and Handbook) names.

FIGURE

FIG. 1: Scheme of the process for extracting the extract with supercritical $CO_2$ according to Example 1.

FIG. 2: Evaluation of the depigmenting effect of the supercritical $CO_2$ extract of white rose obtained according to Example 1.

EXAMPLES

Example 1—Production of a Supercritical $CO_2$ Extract of White Rose

A hybrid variety of rose is obtained by controlled crossing of two varieties: a maternal variety (Tchaikovsky® Meichibon) and a paternal variety (La Rose du Petit Prince/Rose Synactif by Shiseido® Delgramaue).

The maternal line is also known as its plant name: Meichibon. The paternal line is also known as its plant name: Delgramau.

A protocol implemented for obtaining a "supercritical $CO_2$" extract is the protocol described in patent application WO 2012/085366.

Briefly, said protocol consists in obtaining an extract from fresh and/or slightly withered rose flowers, flowering heads and/or leaves according to the invention, comprising the following steps according to which:

a) the rose flowers, flowering heads and/or leaves are picked;

b) said freshly picked flowers, flowering heads and/or leaves are infused in at least one bath comprising an ethanolic solvent, at a temperature of less than 50° C., for example at ambient temperature, so as to obtain an alcoholic mixture (in the case in point an ethanol mixture);

c) said alcoholic mixture is filtered so as to recover an alcoholic floral infusion; and d) an extraction with supercritical $CO_2$ (referred to as $CO_2$sc extraction in FIG. 1) of the alcoholic floral infusion is carried out, at 45° C. and at a pressure of 150 bar, so as to obtain said extract; and The histological quality of the epidermis after treatment was evaluated on the HES-stained histological section in order to determine the effect of the treatment on the epidermis.

The melanocyte physiology was also evaluated in order to detect melanocyte cytotoxicity.

If the active agents tested do not demonstrate any modification in terms of histology or cytotoxicity with respect to melanocytes, the pigmentation is quantified by quantifying the melanin content on the histological section (Fontana-Masson staining) by image analysis.

Microscopic Quantification of Melanin:

The melanin present in the PRE is stained on the histological slide (Fontana-Masson staining) and then quantified by image analysis.

Each epidermis slide is digitized using Nanozoomer®.

For each epidermis, about 10~15 images are extracted (white light, magnification ×20).

The area occupied by melanin is quantified using the Histolab® software.

Statistical Method:

Two parameters, namely graphic comparison (box-plot) and p value significance (Mann-Whitney U test), were applied to the interpretation of the statistical results.

Up to 6 repetitions were calculated for each treatment group.

The statistical significance between the test groups and the corresponding solvent controls was determined using the non-parametric Mann-Whitney U test (n=6).

The statistical significance is defined if the p value is less than 0.05.

All the box-plots and the Mann-Whitney U tests were carried out by means of the SPSS® software.

B) Results

The results are given in Table 1 below and FIG. 2.

TABLE 1

| Topical application | DMSO | Lucinol 300 μM | Lucinol 500 μM | Extract obtained according to Example 1 20 μg/ml | Extract obtained according to Example 1 100 μg/ml |
|---|---|---|---|---|---|
| Number of images | 84 | 85 | 86 | 80 | 84 |
| Mean pixel number/image | 569.02 | 394.69 | 467.76 | 438.76 | 423.26 |
| Standard deviation | 15.18 | 13.38 | 12.74 | 15.63 | 14.34 |
| P value | — | 0.006 | 0.025 | 0.01 | 0.01 | e) said extract is concentrated under moderate vacuum (100 to 500 mbar), at a temperature not exceeding 60° C.

Example 2—Evaluation of the Depigmenting Effect of the Supercritical $CO_2$ Extract of White Rose Obtained According to Example 1

A) Materials and Methods

The extract obtained according to Example 1, dissolved in DMSO, was evaluated by topical application at 20 μg/ml and 100 μg/ml on the reconstructed pigmented Episkin model in a dry incubator.

The results of the evaluation are compared to those of the solvent (DMSO) control and of a reference whitening active agent (Lucinol).

The area occupied by melanin is quantified using the Histolab® software and is represented by the mean pixel number per image. Thus, the higher the mean pixel number per image, the greater the area occupied by melanin.

Conclusion: A decrease in the mean pixel number per image, reflecting a decrease in the area occupied by melanin, is observed with the extract according to Example 1 compared to the DMSO negative control. This decrease is similar to or greater than the decrease observed with the positive control of the study, Lucinol.

Example 3—Depigmenting Emulsion

A depigmenting emulsion having the following composition was prepared:

TABLE 2

| Compounds | % |
|---|---|
| Oily phase | 9 |
| Surfactants | 2 |
| $CO_2$ Extract of Meichibon × Delgramaue Rose | 0.001 |
| Aqueous phase | 40 |
| Polymer | 0.5 |
| Preservatives | qs |
| Alcohol | 3 |
| Water | qs 100 |

The percentage values indicated correspond to mass percentages by weight relative to the total weight of the composition.

The invention claimed is:

1. A method of whitening, lightening and/or depigmenting keratin material comprising applying to the keratin material a whitening, lightening and/or depigmenting agent which is an extract of a hybrid rosebush obtained by the crossing of varieties Meichibon×Delgramaue, wherein said whitening, lightening and/or depigmenting agent is applied in an amount sufficient to obtain whitening, lightening and/or depigmenting of the keratin material.

2. The method of claim 1, wherein said whitening, lightening and/or depigmenting agent is applied in an amount sufficient to obtain whitening of the keratin material.

3. The method of claim 1, wherein said extract of a hybrid rosebush is obtained from flowers, flowering heads and/or leaves of said rosebush.

4. The method of claim 1, wherein said extract of a hybrid rosebush is obtained by extraction with supercritical CO2 of an alcoholic mixture of all or part of said rosebush.

5. The method of claim 4, wherein said alcoholic mixture is obtained after infusion of all or part of said rosebush in at least one bath comprising an alcoholic solvent, at a temperature of less than 50° C., so as to obtain the alcoholic mixture.

6. The method of claim 1, wherein the keratin material is skin.

7. The method of claim 1, wherein said whitening, lightening and/or depigmenting agent is applied in an amount sufficient to obtain lightening of the keratin material.

8. The method of claim 1, wherein said whitening, lightening and/or depigmenting agent is applied in an amount sufficient to obtain depigmenting of the keratin material.

9. A method of depigmenting, lightening and/or whitening keratin material comprising applying a cosmetic composition comprising, in a physiologically acceptable medium, a whitening, lightening and/or depigmenting agent which is an extract of a hybrid rosebush obtained by the crossing of varieties Meichibon x Delgramaue to the keratin material in an amount sufficient to obtain whitening, lightening and/or depigmenting of the keratin material.

10. The method of claim 9, in which said extract of a hybrid rosebush is present in said composition in a concentration of between 0.0001% and 10% by weight relative to the total weight of the composition.

11. The method of claim 9, wherein the keratin material is skin.

12. The method of claim 11, in which said cosmetic composition is applied to the skin of an individual having a dull complexion, a non-uniform complexion, brownish pigmentation blemishes, liver spots, and/or the appearance of a brownish color caused by melanogenesis.

13. The method of claim 9, wherein said whitening, lightening and/or depigmenting agent is applied in an amount sufficient to obtain whitening of the keratin material.

14. The method of claim 9, wherein said extract of a hybrid rosebush is obtained from flowers, flowering heads and/or leaves of said rosebush.

15. The method of claim 9, wherein said extract of a hybrid rosebush is obtained by extraction with supercritical CO2 of an alcoholic mixture of all or part of said rosebush.

16. The method of claim 15, wherein said alcoholic mixture is obtained after infusion of all or part of said rosebush in at least one bath comprising an alcoholic solvent, at a temperature of less than 50° C., so as to obtain the alcoholic mixture.

17. The method of claim 9, wherein said whitening, lightening and/or depigmenting agent is applied in an amount sufficient to obtain lightening of the keratin material.

18. The method of claim 9, wherein said whitening, lightening and/or depigmenting agent is applied in an amount sufficient to obtain depigmenting of the keratin material.

* * * * *